US00PP37026P2

(12) United States Plant Patent
Jimenez

(10) Patent No.: US PP37,026 P2
(45) Date of Patent: Oct. 14, 2025

(54) ***GASTERALOE* PLANT NAMED 'D OVERFLOW'**

(50) Latin Name: *Gasteraloe hybrida*
Varietal Denomination: D OVERFLOW

(71) Applicant: Deltacactus S.L., Amposta (ES)

(72) Inventor: Javier Andres Jimenez, Amposta (ES)

(73) Assignee: DeltaCactus S.L. (ES)

( * ) Notice: Subject to any disclaimer, the term of this patent is extended or adjusted under 35 U.S.C. 154(b) by 0 days.

(21) Appl. No.: 19/195,238

(22) Filed: Apr. 30, 2025

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

(56) References Cited

U.S. PATENT DOCUMENTS

PP30,905 P2 * 9/2019 Jachertz ..... A01H 6/00
Plt./373

* cited by examiner

*Primary Examiner* — Karen M Redden
(74) *Attorney, Agent, or Firm* — Cassandra Bright

(57) ABSTRACT

A new and distinct cultivar of *Gasteraloe* plant named 'D OVERFLOW' is disclosed, characterized by an upright and uniform rosette shape. Foliage is uniquely dark green and densely covered with greyed-green lenticel dots. The new variety is an *Gasteraloe*, typically produced as an ornamental plant.

2 Drawing Sheets

Latin name of the genus and species: *Gasteraloe hybrida.*
Cultivar denomination: 'D OVERFLOW'.

BACKGROUND OF THE INVENTION

The new cultivar is a product of a planned breeding program by the inventor, to produce distinct and better performing varieties. The seed parent is the inventor's own hybrid *Gasteria carinata* #15005-3, unpatented. The pollen parent is the inventor's own hybrid, *Aristaloe aristata* #2001, unpatented. The crossing resulting in the new cultivar was made in 2019 at a nursery in Amposta, Spain. 'D OVERFLOW' was found and selected by the inventor in March 2021 at the same location in Amposta, Spain.

Asexual reproduction of the new cultivar 'D OVERFLOW' was first performed in Amposta, Spain in March 2021, by vegetative cuttings. 'D OVERFLOW' has since produced four generations and has shown that the unique features of this cultivar are stable and reproduced true to type.

SUMMARY OF THE INVENTION

The cultivar 'D OVERFLOW' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'D OVERFLOW'. These characteristics in combination distinguish 'D OVERFLOW' as a new and distinct *Gasteraloe* cultivar:

1. Upright and uniform single rosette.
2. Dark green foliage color with dense greyed-green lenticel dots.

PARENTAL COMPARISONS

Plants of the new cultivar 'D OVERFLOW' are similar to the seed parent in most horticultural characteristics. However, plants of the new cultivar differ in the following:

1. Plants of the new cultivar are rosette-like, having a radial symmetry, while plants of the seed parent are not rosette-shaped, but have a one axis symmetry.

Plants of the new cultivar 'D OVERFLOW' are similar to the pollen parent in most horticultural characteristics. However, plants of the new cultivar differ in the following:

1. Plant habit of the new cultivar is an upright rosette, however the pollen parent has a more upright plant habit.

COMMERCIAL COMPARISONS

'D OVERFLOW' can be compared to the commercial cultivar *Gasteraloe* 'D Delta', U.S. Plant Pat. No. 30,905. The two cultivars are similar in most horticultural characteristics; however, the new cultivar differs in the following:

1. Leaf color of the new cultivar is darker green than foliage color of this comparator.

'D OVERFLOW' can be compared to the unpatented commercial cultivar *Gasteraloe* 'WT01', U.S. Plant Pat. No. 22,012. The two cultivars are similar in most horticultural characteristics; however, the new cultivar differs in the following:

1. Foliage margin of the new cultivar is not as sharp as foliage margin of this comparator.

BRIEF DESCRIPTION OF THE PHOTOGRAPHS

Figure 1:
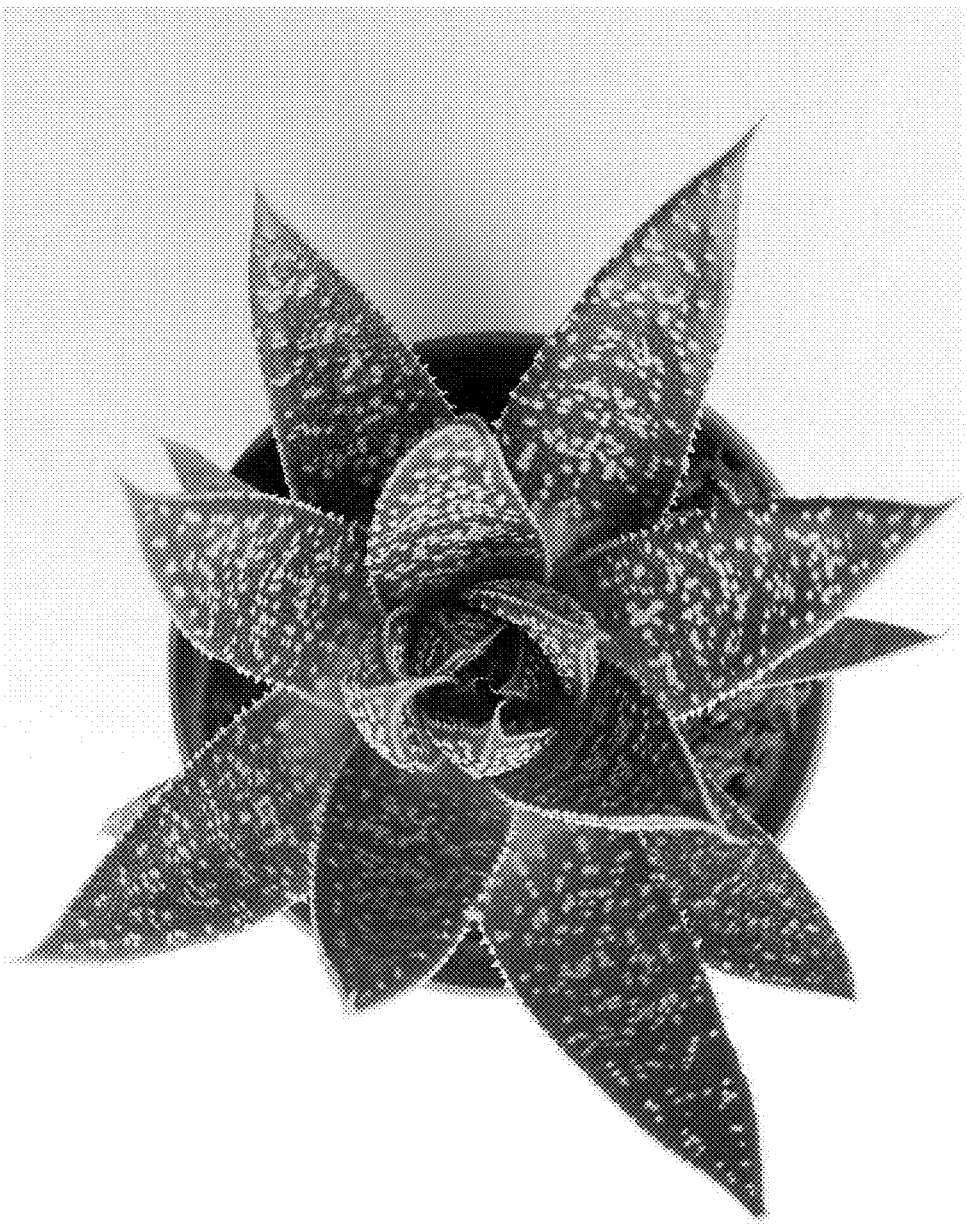

The accompanying photograph in FIG. 1 illustrates in full color a typical plant of 'D OVERFLOW' grown in a greenhouse in Amposta, Spain. This plant is approximately 50 weeks old, shown in a 9 cm container and photographed rom a top down view.

Figure 2:
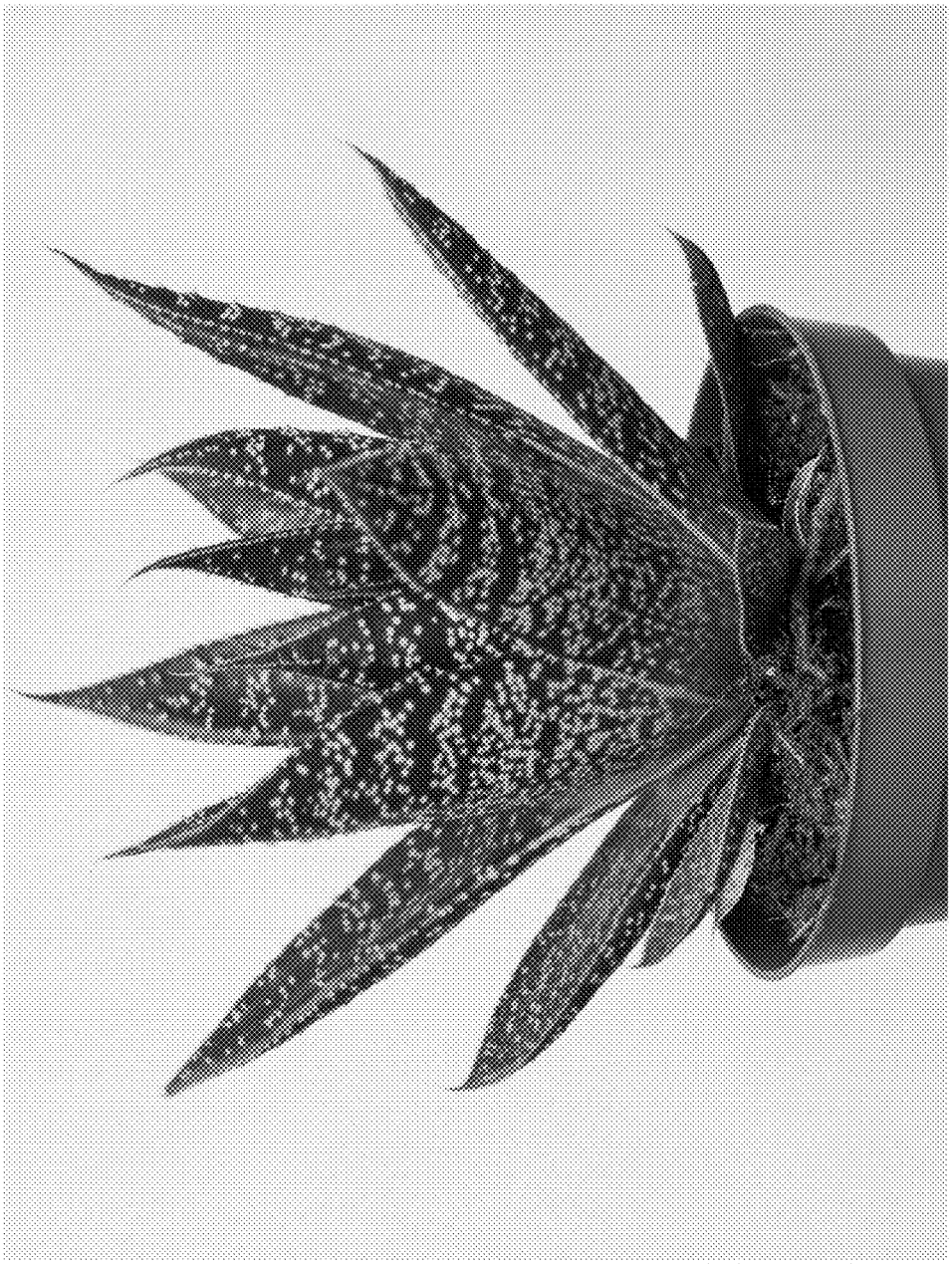

FIG. 2 illustrates a side-view of the same plant.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Color Chart, 2015 edition, except where general terms of ordinary dictionary significance are used. The following observations and measurements describe 'D OVERFLOW' plants in a glass greenhouse in Amposta, Spain. Temperatures ranged from 18° C. to 20° C. during the day, and 15° C. to 18° C. during the night. No artificial light, photoperiodic treatments or chemical treatments were given to the plants. Measurements and numerical values represent averages of typical plant types.

Botanical classification: *Gasteraloe hybrida* 'D OVERFLOW'.

Age of the plant described: 50 weeks.

PROPAGATION

Time to initiate roots: 20 days in summer; 20 days in winter at 20° C.

Time to produce rooted cutting: 80 days in summer; 90 days in winter at 20° C.

Root description: Fibrous, thick, moderately dense and freely-branching. White in color with yellow tips, not accurately measured with The R.H.S. Chart.

Propagation method: Vegetative cuttings.

PLANT

Plant type: Tender perennial potted plant.

Plant shape: Upright broad, V-shape.

Growth habit: Basal rosette.

Container size: 8.5 cm.

Height: Average 10 cm; no flowering observed.

Plant spread: Average 12.8 cm.

Growth rate: Low to moderate. Nearly 1 year to fill a 9 cm pot and larger.

Branching characteristics: Leaves in basal rosettes; 1 basal rosette per plant. No branches or lateral rosettes observed.

FOLIAGE

Leaf:

*Arrangement*.—Single rosette.

*Quantity*.—Average 21 leaves per rosette.

*Average length*.—9.6 cm.

*Average width*.—2.4 cm.

*Thickness*.—7 mm on average.

*Shape of blade*.—Lanceolate.

*Whole leaf aspect*.—Very slightly concave.

*Apex*.—Narrow apiculate with a soft mucronate tip.

*Base*.—Broad cuneate.

*Margin*.—Finely serrate-dentate, average length and height of teeth: 0.5 mm, colored RHS Greyed-Green 190C. Teeth not sharp.

*Texture of top surface*.—Densely pustulate, placed randomly on lamina, as well as loosely arranged in axial lines. Average width: 1 mm, average height 0.1 mm, however, towards distal end of lamina slightly taller, 0.5 mm. Colored RHS Greyed-Green 191C.

*Texture of bottom surface*.—Densely pustulate, placed randomly on lamina, as well as loosely arranged in axial lines. Average width: 1 mm, average height 0.1 mm, however, towards distal end of lamina slightly taller, 0.5 mm. Colored RHS Greyed-Green 191C.

*Pubescence*.—None.

*Rugosity*.—Both sides non-rugose.

*Luster*.—Upper side: Matte. Under side: Matte.

*Color*.—

*Young foliage upper side*.—Green; a blend of NN137B and 141A, fading greyed-yellow towards the base; 161B, moderately pustulate, loosely arranged in axial lines, average diameter: 1.0 mm, average height: less than 0.1 mm, slightly higher towards distal end of lamina: 0.3 mm and less, colored greyed-green; 192D.

*Young foliage under side*.—Green; NN137B, fading greyed-yellow towards the base; 161B, moderately pustulate, loosely arranged in axial lines, average diameter: 1.0 mm, average height: less than 0.1 mm, slightly higher towards distal end of lamina: 0.5 mm and less, colored greyed-green; 192B.

*Mature foliage upper side*.—Greyed-green; N189A, tinged yellow-green; 147A, fading lighter towards the base; 194A and 194B. Lamina densely pustulate, placed randomly on lamina, as well as loosely arranged in axial lines, average diameter: 1.0 mm, average height: less than 0.1 mm, slightly higher towards distal end of lamina: 0.5 mm and less, colored greyed-green; 191C.

*Mature foliage under side*.—Yellow-green to greyed-green; a blend of 147A and N189A, fading yellow-green towards the base; 144A, Base greyed-green; 196C and 196D. Lamina densely pustulate, loosely arranged in axial lines, average diameter: 1.0 mm, average height: less than 0.1 mm, slightly higher towards distal end of lamina: 0.5 mm and less, colored greyed-green; 191C.

*Venation*.—Pattern: Parallel. Color, upper side: Indistinguishable from leaf blade. Color, under side: Indistinguishable from leaf blade.

FLOWER

Flowering not observed to date.

REPRODUCTIVE ORGANS

Not observed to date.

OTHER CHARACTERISTICS

Seeds and fruits: Not observed to date.

Temperature tolerance: Low temperature tolerant to 10 degrees Celsius. High temperature tolerant to 35 degrees Celsius.

Disease/pest resistance: Neither resistance nor susceptibility to the normal disease and pests of *Gasteraloe* has been observed.

What is claimed is:

1. A new and distinct cultivar of *Gasteraloe* plant named 'D OVERFLOW' as herein illustrated and described.

* * * * *